United States Patent
Asahara et al.

(10) Patent No.: US 11,773,376 B2
(45) Date of Patent: Oct. 3, 2023

(54) ARTIFICIAL TENDON OR LIGAMENT TISSUE PRODUCED USING THREE-DIMENSIONAL MECHANOSIGNALING CELL CULTURE SYSTEM

(71) Applicant: National University Corporation Tokyo Medical and Dental University, Tokyo (JP)

(72) Inventors: Hiroshi Asahara, Tokyo (JP); Kensuke Kataoka, Tokyo (JP); Tomoki Chiba, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 588 days.

(21) Appl. No.: 16/630,188

(22) PCT Filed: Jul. 12, 2018

(86) PCT No.: PCT/JP2018/026319
§ 371 (c)(1),
(2) Date: Jan. 10, 2020

(87) PCT Pub. No.: WO2019/013279
PCT Pub. Date: Jan. 17, 2019

(65) Prior Publication Data
US 2021/0115396 A1 Apr. 22, 2021

(30) Foreign Application Priority Data
Jul. 13, 2017 (JP) ................................. 2017-136823

(51) Int. Cl.
| C12N 5/077 | (2010.01) |
| A61L 27/22 | (2006.01) |
| A61L 27/36 | (2006.01) |
| A61L 27/38 | (2006.01) |

(52) U.S. Cl.
CPC ............ *C12N 5/066* (2013.01); *A61L 27/225* (2013.01); *A61L 27/3683* (2013.01); *A61L 27/386* (2013.01); *A61L 27/3834* (2013.01); *A61L 2430/10* (2013.01); *C12N 2506/45* (2013.01); *C12N 2527/00* (2013.01); *C12N 2533/54* (2013.01); *C12N 2533/56* (2013.01)

(58) Field of Classification Search
None
See application file for complete search history.

(56) References Cited

U.S. PATENT DOCUMENTS

2006/0115900 A1* 6/2006 Fujisato ............ A61L 27/3604
435/378
2015/0191699 A1 7/2015 Wang et al.

FOREIGN PATENT DOCUMENTS

| EP | 2984163 | 2/2017 |
| JP | 2011-205964 A | 10/2011 |
| JP | 2015-523083 A | 8/2015 |
| JP | 2016-052272 A | 4/2016 |

OTHER PUBLICATIONS

Hatzmann et al, Cells, 2021, 10:214 (21 pages) (Year: 2021).*
Sasaki et al, Soft Matter, 2010, 6: 1662-1667. (Year: 2010).*
Ahmed et al., "Fibrin: A Versatile Scaffold for Tissue Engineering Applications", Tissues Engineering Part B: Reviews, Department of Cellular and Molecular Medicine, vol. 14, No. 2, Jun. 2008, 19 pages.
Application No. EP18832052.7 et al., Extended European Search Report, dated Mar. 15, 2021, 12 pages.
De La Puente et al., "Cell Culture in Autologous Fibrin Scaffolds for Applications in Tissue Engineering", Experimental Cell Research, vol. 322, No. 1, Mar. 1, 2014, pp. 1-11.
Liu et al., "Current Concepts on Tenogenic Differentiation and Clinical Applications", Journal of Orthopaedic Translation, vol. 9, Apr. 1, 2017, pp. 28-42.
Lu et al., "Tenogenic Differentiation of Mesenchymal Stem Cells and Noncoding RNA: From Bench to Bedside", Experimental Cell Research, vol. 341, No. 2, Feb. 2016, pp. 237-242.
Nixon et al., "Cell-And Gene-Based Approaches to Tendon Regeneration", Journal of Shoulder and Elbow Surgery, vol. 21, No. 2, Feb. 2012, pp. 278-294.
Otabe et al., "Transcription Factor Mohawk Controls Tenogenic Differentiation of Bone Marrow Mesenchymal Stem Cells in Vitro and in Vivo", Journal of Orthopaedic Research, vol. 33, No. 1, Oct. 13, 2014, pp. 1-16.
Breidenbach, et al., "Fibrin Gels Exhibit Improved Biological, Structural, and Mechanical Properties Compared with Collagen Gels in Cell-Based Tendon Tissue-Engineered Constructs," Tissue Engineering, Part A, 2015, vol. 21, Nos. 3 and 4, pp. 438-450.
Rodeheffer, et al., "Identification of White Adipocyte Progenitor Cells In Vivo," Cell, 135, 2008, pp. 240-249.
Lee, et al., "Mechanical properties of decellularized tendon cultured by cyclic straining bioreactor," Journal of Biomedical Materials Research Part A, 2013, vol. 101A, pp. 3152-3158.
Yang, et al., "Enhancement of tenogenic differentiation of human adipose stem cells by tendon-derived extracellular matrix," Biomaterials, 2013, vol. 34, pp. 9295-9306.

(Continued)

*Primary Examiner* — Allison M Fox
(74) *Attorney, Agent, or Firm* — Kilpatrick Townsend & Stockton LLP

(57) ABSTRACT

The present invention relates to providing artificial tendon or ligament tissue having sufficient strength. More specifically, artificial tendon or ligament tissue having sufficient strength is provided by embedding collagen-secreting cells in a gel having strength capable of resisting a tensile load and by culturing the cells while applying a tensile load to the gel to produce artificial tendon or ligament tissue. Cells that steadily express the Mkx gene can be used as the collagen-secreting cells. A fibrin gel containing aprotinin can be used as the gel.

15 Claims, 13 Drawing Sheets

(56) References Cited

OTHER PUBLICATIONS

Qiu, et al., "Cyclic tension promotes fibroblastic differentiation of human MSCs cultured on collagen-fibre scaffolds," Journal of Tissue Engineering and Regenerative Medicine, 2016, vol. 10, pp. 989-999.
Asahara, et al., "Tendons and Ligaments: Connecting Developmental Biology to Musculoskeletal Disease Pathogenesis," Journal of Bone and Mineral Research, 2017, vol. 32, pp. 1773-1782.
Nakamichi, et al., "Mohawk promotes the maintenance and regeneration of the outer annulus fibrosus of intervertebral discs," Nature Communications, 2016, 16(7), 12503, pp. 1-14.
Kapacee, et al. "Synthesis of embryonic tendon-like tissue by human marrow stromal/mesenchymal stem cells requires a three-dimensional environment and transforming growth factor $\beta 3$" Matrix Biol. 2010, 29(8), pp. 668-677.
Liu, et al., "Mohawk Promotes the Tenogenesis of Mesenchymal Stem Cells Through Activiation of the TCF$\beta$ Signaling Pathway," Stem Cells 2015, 33(2), pp. 443-455.
Chen, et al., "Force and scleraxis synergistically promote the commitment of human ES cells derived MSCs to tenocytes," Scientific Reports 2012, 2:977, pp. 1-12.
International Preliminary Report on Patentability, dated Jan. 16, 2020 in PCT/JP2018/026319, 9 pages.

\* cited by examiner

ARTIFICIAL TENDON OR LIGAMENT TISSUE PRODUCED USING THREE-DIMENSIONAL MECHANOSIGNALING CELL CULTURE SYSTEM

CROSS-REFERENCE TO RELATED APPLICATIONS

This application is an application claiming the priority of Application No. 2017-136823 (filing date: Jul. 13, 2017), which is incorporated herein in its entirety by reference.

TECHNICAL FIELD

The present invention relates to an artificial tendon/ligament-like tissue and a method of manufacturing thereof. More specifically, it relates to artificial tendon/ligament-like tissues produced using a three-dimensional mechano-signaling cell culture system. The present invention also relates to a method of producing an artificial tendon/ligament-like tissue using a three-dimensional mechano-signaling cell culture system, and a composition for use thereof.

BACKGROUND ART

Tendons/ligaments are tissues that exert a function by connecting muscles and bones accurately and resiliently, and damage and diseases thereof significantly impair patients' daily lives. Movement disorder is a major obstructive factor to healthy life expectancy, and the fact that it accounts for about 20% of the contributing factors of nursing in elderly people, which is comparable to dementia and stroke, makes regeneration and reconstruction of tendons and ligaments an urgent issue in the super-aging society in the future.

In addition, tendon/ligament injury is a major factor that threatens athletes' career as a player. Therefore, tendon/ligament regeneration and reconstruction are much needed in the field of sports medicine.

However, developmental studies of tendons/ligaments and regenerative medicine have not fully advanced to date because for a long time the tissue-specific master gene was not known.

Through analysis of the tendon/ligament tissue-specific gene expression patterns, a transcription factor, Mohawk (Mkx), was identified and it was elucidated that Mkx is indispensable for the tendon/ligament formation from an analysis using the Mkx knockout mouse (Patent Document 1). C3H10T1/2, a murine mesodermal stem cell line transfected with the Mkx gene by retrovirus, strongly expresses the tendon/ligament cell gene marker Scleraxis, decorin, and type I collagen as compared with the control group (Non-patent Document 1).

The major component of tendon is an extracellular matrix composed of type I collagen and proteoglycans. However, the formation of structurally meaningful tendon tissue in vivo requires correct orientation of collagen fibers and tendon cells, and mere transplantation of Mkx-expressing cells into the body may be insufficient for regenerating tissues for regenerative medicine.

CITATION LIST

Patent Documents

Patent Document 1: JP 2011-205964

Non-Patent Documents

Non-patent Document 1: Nakamichi R et al. 2016 Nat Commun. 16 (7) 12503
Non-patent Document 2: Kapacee Z et al. 2010 Matrix Biol. 29 (8) 668-77
Non-patent Document 3: Liu H et al. 2015 Stem Cells. 33 (2) 443-55
Non-patent Document 4: Chen X et al. 2012 Sci Rep. 2:977.

SUMMARY OF THE INVENTION

Problems to be Solved by the Invention

One of the objectives of the present invention is to provide an artificial tendon/ligament-like tissue and a method of manufacturing thereof. Another objective of the present invention is to provide a composition for use in a method of manufacturing an artificial tendon/ligament-like tissue.

Means for Solving the Problems

The present inventors have found that by embedding cells transfected with the Mkx gene, e.g., by retrovirus, in a fibrin gel added with aprotinin and culturing them under tension, an artificial tissue with collagen fibers and cells oriented parallel to the direction of elongation (longitudinal direction) can be formed. The present inventors also found unexpectedly, that cells in the $CD24^+CD34^+$ fraction exhibited a stronger tendon ligament gene-expression pattern than cells in the other fractions.

The present invention is based on such findings and encompasses the following embodiments:
 [1] A method of manufacturing an artificial tendon/ligament-like tissue comprising: (a) embedding a collagen-secreting cell in a gel that is strong enough to withstand a tensile load, and (b) culturing the cell while applying a tensile load to the gel.
 [2] The method according to [1], wherein the collagen-secreting cell is a cell that constitutively expresses the Mkx gene.
 [3] The method according to [1] or [2], wherein the collagen-secreting cell is a cell that has been transfected with a vector to introduce the Mkx gene.
 [4] The method according to any of [1] to [3], wherein the cell is a C3H10T1/2 cell, a cell line, a normal cell, a cell derived from a tissue stem cell, a cell derived from an ES cell, or a cell derived from an iPS cell.
 [5] The method according to any of [1] to [4], wherein the cell is CD24 positive and CD34 positive.
 [6] The method according to any of [3] to [5], wherein the vector is a retroviral vector.
 [7] The method according to any of [1] to [6], wherein the gel is a fibrin gel.
 [8] The method according to any of [1] to [7], wherein the gel contains a plasmin inhibitor.
 [9] The method according to any of [1] to [8], wherein the gel contains aprotinin.
 [10] The method according to any of [1] to [9], wherein the tensile load is at least 2% extension per day.

[11] The method according to any of [1] to [10], comprising further (c) performing a decellularization treatment.
[12] The method according to [11], wherein the decellularization treatment comprises microwave irradiation.
[13] An artificial tendon/ligament-like tissue, having collagen fibers with an orientation parallel to the longitudinal direction.
[14] An artificial tendon/ligament-like tissue, having a tensile strength of at least 50 kPa.
[15] The artificial tendon/ligament-like tissue according to [13] having a tensile strength of at least 50 kPa.
[16] The artificial tendon/ligament-like tissue according to any of [13] to [15] comprising type I collagen.
[17] The artificial tendon/ligament-like tissue according to any of [13] to [16], comprising a cell transfected with the Mkx gene using a vector.
[18] An artificial tendon/ligament-like tissue manufactured using the method according to any of [1] to [12] above.
[19] The artificial tendon/ligament-like tissue according to any of [13] to [17], produced using the method according to in any of [1] to [12] above.
[20] A three-dimensional cell culture medium composition comprising fibrinogen and aprotinin for use in the method according to any of [1] to [10].
[21] A method of producing an artificial tendon/ligament-like tissue comprising: (a) embedding in a gel a cell that is CD24 positive and CD34 positive, and (b) culturing the cell while applying a tensile load to the gel.
[22] The method according to [21], wherein the cell is a cell derived from a tissue stem cell, a cell derived from an ES cell, or a cell derived from an iPS cell.
[23] The method according to [22], further comprising inducing differentiation of the cell into a mesodermal stem cell.
[24] The method according to any of [21] to [23], further comprising isolating the cell that is CD24 positive and CD34 positive.
[25] A cellular composition comprising mesodermal stem cells that are CD24 positive and CD34 positive.
[26] The cellular composition according to [25], wherein the purity of $CD24^+CD34^+$ mesodermal stem cells is at least 85%.
[27] The cellular composition according to [25] or [26] comprising at least 5×10 5 cells.
[28] The cellular composition according to any of [25] to [27], wherein the mesodermal stem cell is a cell derived from an iPS cell.
[29] The cellular composition according to any of [25] to [28], wherein the mesodermal stem cell is a human cell.
[30] The cellular composition according to any of [25] to [29], wherein the mesodermal stem cell is a genetically modified cell.
[31] The cellular composition according to any of [25] to [30], which is frozen.
[32] The cellular composition according to any one of [25] to [31], which is enclosed in a single container.

The right column is an artificial tendon ligament-like tissue using CD24$^+$CD34$^+$ cells transfected with Mkx.

Figure 12:
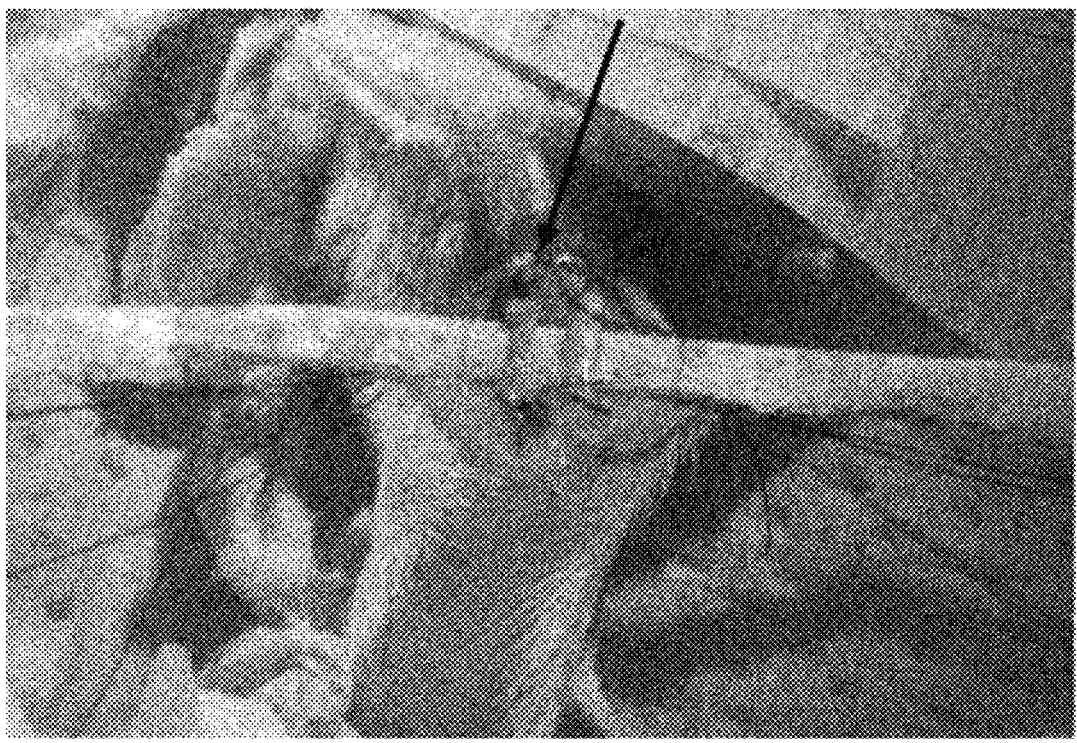

FIG. 12 shows a photograph during the operation of transplanting an artificial tendon ligament-like tissue derived from CD24$^+$CD34$^+$ IPS-MSCs with forced Venus-Mkx expression, which have been treated with decellularization and nuclear lavage, into the site of total resection of Achilles tendon on the gastrocnemius muscle side in a rat model of total Achilles tendon resection on the gastrocnemius muscle side. The black arrow shows the transplanted artificial tendon ligament-like tissue derived from CD24$^+$CD34$^+$ IPS-MSCs with forced Venus-Mkx expression.

Figure 13:
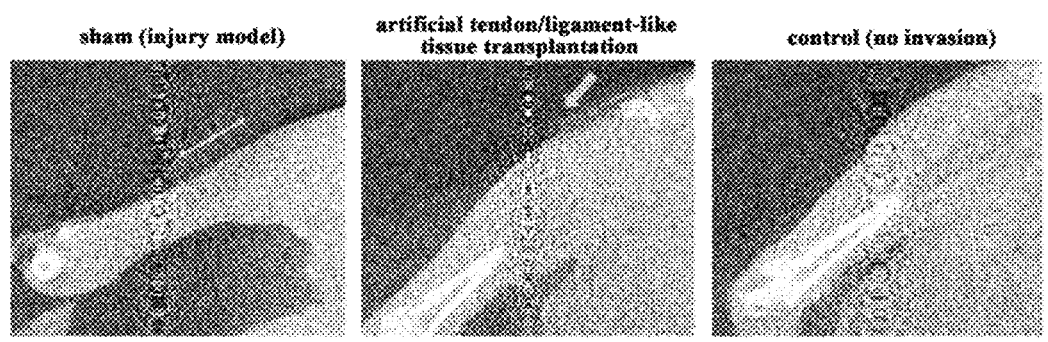

FIG. 13 is an image of non-invasive imaging analysis of the lesion site performed using a microfocus X-ray device (Shimazu, Inc., inspeXio SMX-100CT) in a rat injury model in which the central part of the Achilles tendon on the gastrocnemius muscle side of the left hind limb was totally resected, with the rat under general anesthesia for one week after the living-donor transplantation experiment. The bidirectional arrow in the sham group (injury-model group) indicates the area of low x-ray absorption in the Achilles tendon. The arrow in the transplantation group of artificial tendon ligament-like tissue derived from CD24$^+$CD34$^+$ IPS-MSCs with forced Venus-Mkx expression indicates uniform radiolucency at the transplantation site.

MODE FOR CARRYING OUT THE INVENTION

As described above, the present inventors have found that cells transfected with the Mkx gene, for example by retrovirus, can be embedded in a fibrin gel with aprotinin and cultured under tension to form an artificial tissue presenting an orientation of collagen fibers and cells parallel to the direction of elongation (longitudinal direction). The present inventors also found unexpectedly that cells in the CD24$^+$CD34$^+$ fraction exhibited a stronger tendon ligament gene expression pattern than cells in the other fractions.

Artificial Tendon/Ligament-Like Tissue

A tendon/ligament-like tissue refers to a strong connective tissue composed mainly of oriented type I collagen in vivo. Examples include tendons, ligaments, annulus fibrosus, periodontal ligaments, and such.

Tendons are tissues that connect bones with muscles and transmit muscle contractions to bones. Tendon damage is generated by injury, aging and such; however, the tendon is a tissue of which regeneration is difficult as it lacks feeding blood vessels, and development of novel tendon injury therapy such as regenerative medicine is desired. The constituents of tendon are primarily extracellular matrix and tendon cells. Extracellular matrix is produced by tendon cells and includes collagen (type I collagen as a major component; type III collagen, type V collagen and such as minor collagens) and proteoglycans (decorin, fibromodulin, biglycan, lumican and such).

Ligaments are short bundles of tough connective tissue that connect bones to form joints. The main component is the type I collagen-centric long collagen fiber. Ligaments also work to limit the range of motion of joints. Ligaments are similar to tendons and fascia in that they are made up of connective tissues, but they are joined differently. Ligaments connect one bone to another bone, whereas tendons connect muscles to bones, and fascia connect muscles to other muscles. All of these are found in the skeletal system of the human body. Ligaments usually do not regenerate spontaneously.

The annulus fibrosus is a ligament-like structure that joins a vertebral body to a vertebral body in the spine. Similar to tendons/ligaments, its principal components are oriented type I collagen and proteoglycans. Since humans perform erect bipedal walking, the intervertebral discs constantly bear the load of one's own weight. Deformity of the intervertebral discs due to aging or excessive pressure is known as disc herniation. Therapy consists only of anti-inflammatory agents and surgical removal of the deformed area, and no method of disc regeneration has been discovered to date.

The periodontal ligament is a connective tissue that connects the root to the alveolar bone. The periodontal ligament holds the tooth in the alveolar bone and serves to relieve pressure on the tooth during mastication. Similar to tendon/ligament, its main components are type I collagen and type III collagen. It is known that undifferentiated mesenchymal stem cells with the ability to differentiate into various periodontal tissue cells are engrafted in the periodontal ligament, and regenerative medicine is under consideration for cases of loss of periodontal ligament due to tooth extraction or periodontal disease.

The artificial tendon/ligament-like tissue according to the present invention can be prepared by three-dimensional culture of collagen-secreting cells under tensile load. In one embodiment, the artificial tendon/ligament-like tissue according to the present invention has collagen fibers with an orientation parallel to the longitudinal direction. This orientation of collagen fibers is important for the intensity of the artificial tendon/ligament-like tissue. The collagen fiber orientation does not require that all the collagen fibers are strictly parallel in the longitudinal direction. Also, in one embodiment, the artificial tendon/ligament-like tissue according to the present invention has a tensile strength of, for example, 25 kPa or more, 30 kPa or more, or 35 kPa or more, preferably at least 50 kPa. Tensile strength can be measured, for example, by a break test using a creep meter. Sufficient strength is necessary for the produced artificial tendon/ligament-like tissue to be transplanted into the living body to function. The artificial tendon/ligament-like tissue according to the present invention may be used in a treatment method comprising the step of transplanting the produced artificial tendon/ligament-like tissue into a human or non-human. Intensity can also be increased by bundling multiple artificial tendon/ligament-like tissues produced by the method of the present invention. For the collagen-secreting cell, for example, a cell which steadily expresses the Mkx gene can be used. Such cells can be prepared, for example, by introducing the Mkx gene into mesodermal stem cells using vectors.

Mohawk (Mkx) Gene

Mkx (Mohawk; Irxl1) is a homeobox-type transcription factor expressed in tendons during the embryonic stage. Mkx is a recently discovered transcription factor classified into the TALE superclass of atypical homeobox genes (Anderson D M et al. (2006). Dev Dyn 235(3) p. 792-801). Mkx has been reported to be expressed in tendons, muscles, cartilage precursors, male gonads, and renal ureteroblast tips. It has also been reported as a transcription factor expressed in tendons during the construction of a whole-mount in situ hybridization database (EMBRYS) of 1520 transcription factors and transcription cofactors using E9.5, E10.5, and E11.5 murine embryos (Yokoyama S et al. 2009 Dev Cell 17(6) p 836-848). Overexpression of the Mkx gene increases the expression of type I collagen, a major component of the tendon, and proteoglycans which promote collagen bundle formation, suggesting that Mkx is important in the process of tendon maturation.

Information about the human Mkx protein is available on NCBI as Accession No. NP_775847. The Mkx protein is a protein of 352 amino acids. Information about the human Mkx gene is also available on NCBI as Accession No. NM_173576. The human Mkx gene, located on human chromosome 10, consists of about 3658 base pairs in total length and consists of seven exons. The murine Mkx gene is available on NCBI as Accession No. NM_177595.

Collagen-Secreting Cells

For the collagen-secreting cells, for example, cells constitutively expressing the Mkx gene or cells with high expression of the endogenous Mkx gene can be used. Secreted collagen includes at least type I collagen. Such cells can be prepared, for example, by introducing the Mkx gene into mesodermal stem cells using vectors. Mesodermal stem cells may be derived from iPS cells. For example, retroviral vectors, adeno-associated virus (AAV) vectors, adenoviral vectors, lentiviral vectors, plasmid vectors, and phage vectors may be used, but any vector known to those skilled in the art may be appropriately selected for use. Cells, for example, mesodermal stem cells derived from pluripotent stem cells such as, for example, established mesodermal stem cells (mouse C3H10T1/2 cells, etc.), mesodermal stem cells derived from a living organism (human bone marrow-derived mesodermal stem cells, etc.), and iPS cells (preferably human iPS cells) can be used; and cells isolated from live tendon and ligament tissues (CD24$^+$CD34$^+$ tendon ligament-derived cells) are assumed to be an example of cells with high Mkx gene expression, but any cells known to those skilled in the art can be selected appropriately for use. The cell can be, for example, a C3H10T1/2 cell, a cell line, a normal cell, a cell derived from a tissue stem cell, a cell derived from an ES cell, or a cell derived from an iPS cell. As used herein, the term "cell-derived cell" includes the original cell itself, e.g., "a cell derived from a tissue stem cell" includes the tissue stem cell itself. In one embodiment, for example, the cell is an iPS-derived CD24$^+$CD34$^+$ cell. For the CD24$^+$CD34$^+$ cells, those isolated by any method such as FACS may be used. It should be noted that the Mkx gene used in the present invention does not necessarily have a wild-type sequence and may have permissible mutations (e.g., substitutions, deletions, insertions of one to several amino acids).

One embodiment of the present invention relates to a method of producing an artificial tendon/ligament-like tissue comprising: (a) embedding cells that are CD24 positive and CD34 positive in a gel; and (b) culturing the cells while applying a tensile load to the gel. The cell may be a cell derived from a tissue stem cell, a cell derived from an ES cell, or a cell derived from an iPS cell. The present inventors unexpectedly found that cells in the CD24$^+$CD34$^+$ fraction exhibited a stronger tendon ligament gene-expression pattern than cells in the other fractions. CD24 is a sialoglycoprotein expressed on the surfaces of most B lymphocytes and differentiating neuroblasts. This protein is also expressed in neutrophils and neutrophil progenitor cells. The CD34 protein is a member of the single-pass transmembrane sialomucin protein family and is expressed in early-stage hematopoietic tissues and blood vessel-associated tissues.

In addition, in one embodiment of the present invention, differentiation induction of the cells into mesodermal stem cells is further performed in the method of producing an artificial tendon/ligament-like tissue. For example, induction of differentiation into mesodermal stem cells can be performed using retinoic acid by referring to the method described in literature (Takashima Y et al. 2007 Cell. 129(7) 1377-88).

In addition, in one embodiment of the present invention, isolation of cells that are CD24 positive and CD34 positive is further performed. Isolation can be performed, for example, by using FACS, without being limited thereto. For flow cytometry, for example, the Beckman-Coulter MoFlo XDP can be used. The FACS gating conditions can be adjusted depending on the number and purity of cells required.

Cellular Composition

One embodiment of the present invention relates to a cellular composition comprising mesodermal stem cells that are CD24 positive and CD34 positive. Such cells may be preferably used in a method of producing an artificial tendon/ligament-like tissue in accordance with the present invention. The cellular composition comprises at least $10^5$, e.g., $10^6$ or more, preferably $10^7$ or more, more preferably $10^8$ or more, more preferably $10^9$ or more mesodermal stem cells. The cellular composition may contain cells other than mesodermal stem cells, but preferably there is a high purity of the mesodermal stem cells. The purity of mesodermal stem cells in the cellular composition is at least 50%, preferably 80% or more, more preferably 85% or more, 90% or more, or 95% or more. The cells contained in the cellular composition are preferably, but not limited to, human cells. In one embodiment of the invention, the cellular composition comprising mesodermal stem cells is enclosed in a single container.

The mesodermal stem cells contained in the cellular composition may be cells in which a gene has been modified by introduction of the gene using vectors such as retroviral vectors, or by genome-editing techniques such as CRISPR/Cas. The mesodermal stem cells may be cells derived from iPS cells. For example, the mesodermal stem cells contained in the cellular composition may have an amplified expression of the Mkx gene.

Also, one embodiment of the present invention relates to vials or containers containing at least $5 \times 10^5$, e.g., $10^6$ or more, preferably $10^7$ or more, more preferably $10^8$ or more, more preferably $10^9$ or more mesodermal stem cells. Vials or containers may be glass or plastic. Cells in vials or containers may be frozen or semi-frozen.

Cell Culture

In producing an artificial tendon/ligament-like tissue according to the present invention, cells can be embedded in a gel and cultured in three dimensions. A fibrin gel can be used for the gel. The fibrin gel preferably contains a protease inhibitor. Examples of the protease inhibitor include plasmin inhibitors and elastin inhibitors. As a plasmin inhibitor, for example, aprotinin, α2-antiplasmin, ε-aminocaproic acid and such can be used. As an elastin inhibitor, for example, Elastatinal can be used. By including a protease inhibitor such as aprotinin in the gel, it is possible to maintain the strength of the gel in cell culture and when transplanting into a living body. Concentrations of a protease inhibitor such as aprotinin range, for example, from 0.1 mg/ml to 10 mg/ml, preferably from 0.3 mg/ml to 3 mg/ml.

In the manufacture of an artificial tendon/ligament-like tissue according to the present invention, the three-dimensional cell culture can be performed under tensile load, and therefore the gel used for cell culture is required to have a strength that can withstand the tensile load. Gels with an intensity that can withstand the tensile load can be obtained by mixing fibrinogen, thrombin, and aprotinin to prepare an aprotinin-containing fibrin gel, for example, as described in the examples of the present application, without being limited thereto. In one embodiment, for example, a collagen gel is used. As used herein, a system for culturing cells in three dimensions (e.g., in a hydrogel) under tensile load (stretch tension) is referred to as a "three-dimensional mechano-signaling cell culture system". Tensile load can be performed using any method known to those skilled in the art, and it can be performed using, for example, Shelpa (Menicon Life Science), STB-140 (Strex, Inc.). Tension can be, for example, 0.2-20% extension per day, preferably at least 2% extension. The extension rate is defined as the rate of increase of the chamber width after stretch relative to the pre-stretch state of the three-dimensional culture chamber. More specifically, it is calculated from the extension rate (%)=(post-stretch chamber width−pre-stretch chamber width)/(pre-stretch chamber width×100). The period of mechano-signaling cell culture is, for example, at least 8 hours per day, preferably 16 hours per day. Cells are typically cultured for 7 to 30 days. It is desirable that the stretch load is carried out with a gradual increase of the extension rate each day.

Decellularization Treatment

Decellularization can be performed to eliminate viable cells contained in the artificial tendon/ligament-like tissues produced by three-dimensional mechano-signaling cell culture. The decellularization treatment can be performed by any method known to those skilled in the art, and it can be performed, for example, by high hydrostatic pressure treatment, surfactant treatment, microwave irradiation, and such.

Medium Composition

One embodiment of the present invention relates to a culture medium composition containing fibrinogen and aprotinin for three-dimensional cell culture for use in the manufacture of an artificial tendon/ligament-like tissue. Details of an exemplary manufacturing method are as described above. The medium composition for three-dimensional cell culture contains at least fibrinogen and thrombin, and preferably contains a protease inhibitor. The medium composition for three-dimensional cell culture may contain, for example, 1 mg/ml to 30 mg/ml of fibrinogen, 0.1 mg/ml to 10 mg/ml of aprotinin, and/or 0.01 mg/ml to 3 mg/ml of thrombin; preferably 5 mg/ml to 10 mg/ml of fibrinogen, 0.3 mg/ml to 3 mg/ml of aprotinin, and/or 0.1 mg/ml to 1 mg/ml of thrombin. The culture medium composition for three-dimensional cell culture of the present invention may contain additional components to enhance the strength of the gel. The three-dimensional cell culture medium composition of the present invention may also further include common culture medium components used for cell culture. One embodiment of the present invention includes a kit that comprises fibrinogen and aprotinin, and possibly also a protease inhibitor for use in the manufacture of an artificial tendon/ligament-like tissue.

The following examples illustrate the invention, but these are not intended to limit the invention in any way.

EXAMPLES

Example 1: Generation of an Artificial Tendon Ligament-Like Tissue Using C3H10T1/2

A retrovirus vector was used to forcedly express the Venus-Mkx fused gene in C3H10T1/2 cells. After concentrating only the cells with forced Venus-Mkx expression by drug selection, Fibrinogen (SIGMA, F3879-1G), Thrombin (SIGMA, T6884-250UN), and Aprotinin (Wako, 010-23581) were adjusted to the final concentrations of 8.3 mg/ml, 33 U/ml, and 0.3 mg/ml, respectively, and the cells with forced Venus-Mkx expression ($1\times10^7$ cells) were suspended using this mixture solution. As a subject of comparison, Venus was forcedly expressed in C3H10T1/2 using the retrovirus vector, and drug-selected cells were used.

The mixture of gel and cells was injected into a three-dimensional stretch culture chamber (Strex, STB-3.5GS), incubated at 37° C. for 30 min in 5% $CO_2$, and turned into a gel. After gelation, a MEMα medium containing 10 v/v % FBS, 1 v/v % penicillin/streptomycin was added to the chamber. After further incubation at 37° C. and 5% $CO_2$ for 18 hours to increase the strength of the gel, stretching was performed using a cell-stretching device (Strex, STB-140). The stretch load was carried out for 1 week, while the extension rate was gradually increased. Specifically, it was 2% (Day 1), 4% (Day 2), 5% (Day 3), 8% (Day 4), and 10% (Days 5-7), with a stretch time of 18 hours/day.

Figure 1:
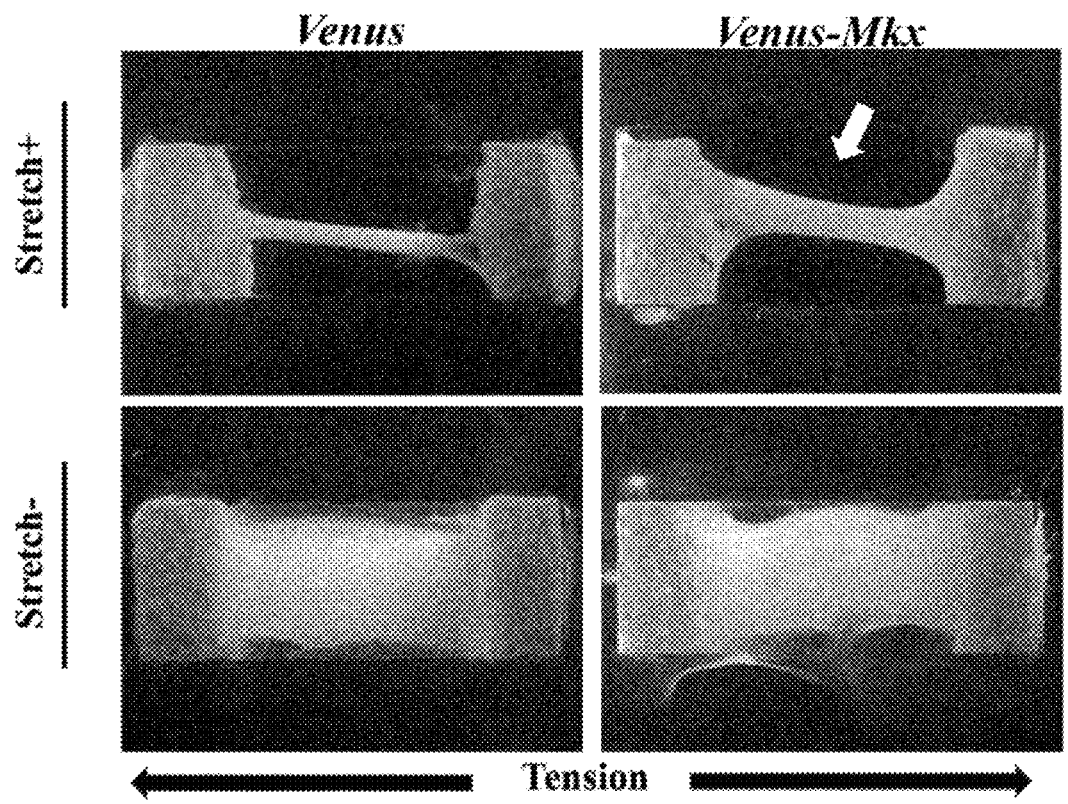
FIG. 1 is a photograph showing an artificial tendon ligament-like tissue derived from C3H10T1/2 produced in a three-dimensional mechano-signaling cell culture system. The upper row has tensile load, and the lower row has no tensile load. The left column shows cells transfected with the control and the right column shows cells transfected with Mkx.

The produced artificial tendon ligament-like tissue is shown in FIG. 1 (see arrow). An artificial tendon ligament-like tissue is produced in the artificial tendon ligament-like tissue which has been applied with a stretch load using cells with forced Venus-Mkx expression (FIG. 1).

Figure 2:
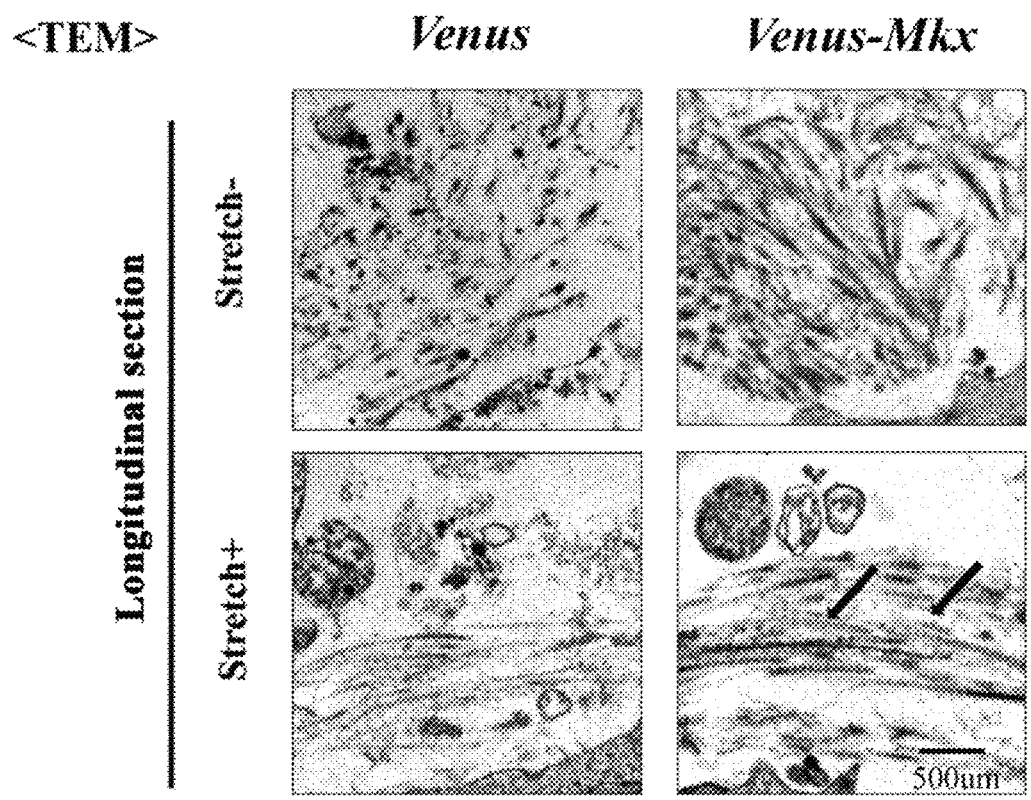
FIG. 2 is a photograph showing a vertical cross-sectional view of an artificial tendon ligament-like tissue derived from C3H10T1/2. The upper row has tensile load, and the lower row has no tensile load. The left column shows cells transfected with the control and the right column shows cells transfected with Mkx.

Longitudinal sections of the artificial tendon ligament-like tissue were observed by electron microscopy (Hitachi, S-4500). In the artificial tendon-ligament-like tissue applied with a stretch load using cells with forced Venus-Mkx expression, collagen fiber bundles parallel to the direction of extension were identified (FIG. 2, see arrows).

Figure 3:
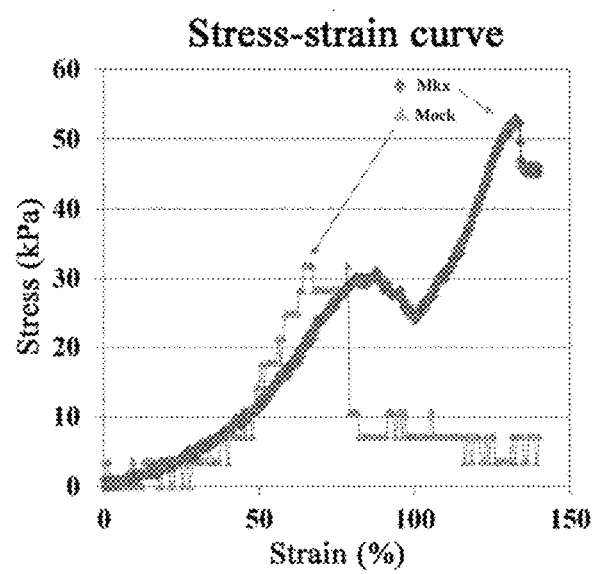
FIG. 3 shows the stress-strain curve of an artificial C3H10T1/2-derived tendon ligament-like tissue during the intensity load test. The vertical axis indicates stress (Stress), and the horizontal axis indicates strain (Strain). It has been shown that the breaking load was 52 kPa in the artificial tendon ligament-like tissue (Mkx) and 31 kPa in the control group (Mock) applied with a stretch load using cells with forced Venus-Mkx expression.

Intensity load test of the artificial tendon ligament-like tissue was carried out using a creep meter (Yamazaki, RE-33005B). The breaking load was 52 kPa in the artificial tendon ligament-like tissue applied with a stretch load using cells with forced Venus-Mkx expression, whereas it was 31 kPa in the control (FIG. 3).

Example 2: Artificial Tendon Tissue Formation by Mkx+Mechanostress Using a Collagen Gel A retrovirus vector was used to forcedly express the Venus-Mkx fused gene in C3H10T1/2 cells. After concentrating only cells with forced Venus-Mkx expression by drug selection, 10 v/v % Collagen neutralize buffer (Nitta gelatin, Cellmatrix Type1-A), 10 v/v % MEMα (Gibco 12000-063 was suspended in DDW to make 10× the specified concentration), 10 v/v % FBS, 1 v/v % 100×NEAA (Gibco 11140-050), 1 v/v % GlutaMAX (Gibco 35050-061), and 1 v/v % 100× Pen Strep (Gibco 15140-122) were added to the collagen gel (Nitta gelatin, Cellmatrix Type1-A) to achieve the respective final concentrations described above. Further, by referring to literature (Laflamme, M A. et al. 2007 Nat Biotechnol. 25(9) 1015-24), the final concentrations of Z-VAD-FMK (G723A, PROMEGA, Bcl-Xl BH4 4-23 (197217-1MG, Calbiochem), Ciclosporin A (039-16301, Wako), Murine IGF-1 (250-19, PeoroTech), and Pinacidil monohydrate (sc-203198, ChemCruz) were adjusted to 100 mM, 50 nM, 200 nM, 100 ng/ml, and 50 mM, respectively, in order to enhance cell viability in the three-dimensional culture. This mixture solution was used to suspend cells with forced Venus-Mkx expression ($5\times10^5$ cells). As a subject of comparison, Venus was forcedly expressed in C3H10T1/2 using the retrovirus vector, and the drug-selected cells were used.

The mixture of gel and cells was injected into a three-dimensional stretch culture chamber (Strex, STB-3.5GS), incubated at 37° C. for 30 min in 5% $CO_2$, and turned into a gel. After gelation, an MEMα medium containing 10 v/v % FBS, 1 v/v % penicillin/streptomycin, 1 v/v % GlutaMAX (Gibco 35050-061, 1 v/v % 100×NEAA (Gibco 11140-050), and 55 µM 2-mercaptoethanol (Gibco 21985-023) was added to the chamber. After further incubation at 37° C. and 5% $CO_2$ for 18 hours to increase the intensity of the gel, stretching was performed using a cell-stretching device (Menicon Life Science, Shellpa Pro). The stretch load was carried out for 1 week, while the extension rate was gradually raised. Specifically, it was 2% (Day 1), 4% (Day 2), 5% (Day 3), 8% (Day 4), and 10% (Days 5-7), with a stretch time of 18 hours/day.

Figure 4:
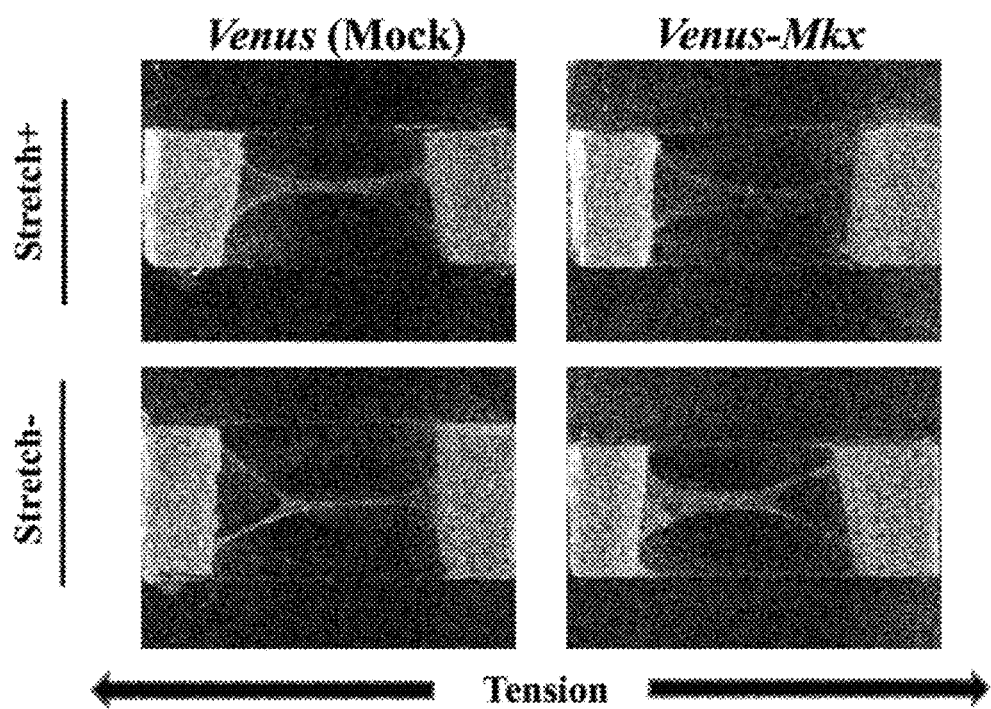
FIG. 4 is a photograph showing an artificial C3H10T1/2-derived tendon ligament-like tissue produced using collagen gel in a three-dimensional mechano-signaling cell culture system. The upper row has tensile load, and the lower row has no tensile load. The left column shows cells transfected with the control and the right column shows cells transfected with Mkx.

The prepared artificial tendon ligament-like tissue is shown. An artificial tendon ligament-like tissue is produced in the artificial tendon ligament-like tissue applied with a stretch load using cells with forced Venus-Mkx expression (FIG. 4).

Decellularization was performed on the artificial tendon ligament-like tissue using the high hydrostatic pressure method. Specifically, a cold isotropic pressure processing equipment (Kobe steel, Dr. CHEF) was used to press at 10,000 atmospheres, 15 minutes, and 10° C. After compression, the nuclei were washed with DNase (1 v/v % 10×DNase I Buffer (Takara Bio, 2270A), 10 U/ml Recombinant DNase I (RNase-free) (Takara Bio, 2270A), 1 v/v % penicillin/streptomycin) for three days and removed. Then, the DNase solution was washed with physiological saline for another three days, and the solution was removed.

For the artificial tendon-ligament-like tissue, cross-linking of the decellularized artificial tissue was performed to improve the stability of the artificial tissue in the body, by referring to literature (Nam, K. et al. 2009 J Artif Organs. 12(1) 47-54). The reaction was performed for 24 hours (in a 4° C. rotator) in a cross-linking reaction solution of 30% v/v ethanol/DDW, 70 mM EDC (wako 348-03631), and 70 mM NHS (wako 089-04032). Then, the reaction solution was removed by washing with DDW for one day.

Figure 5:
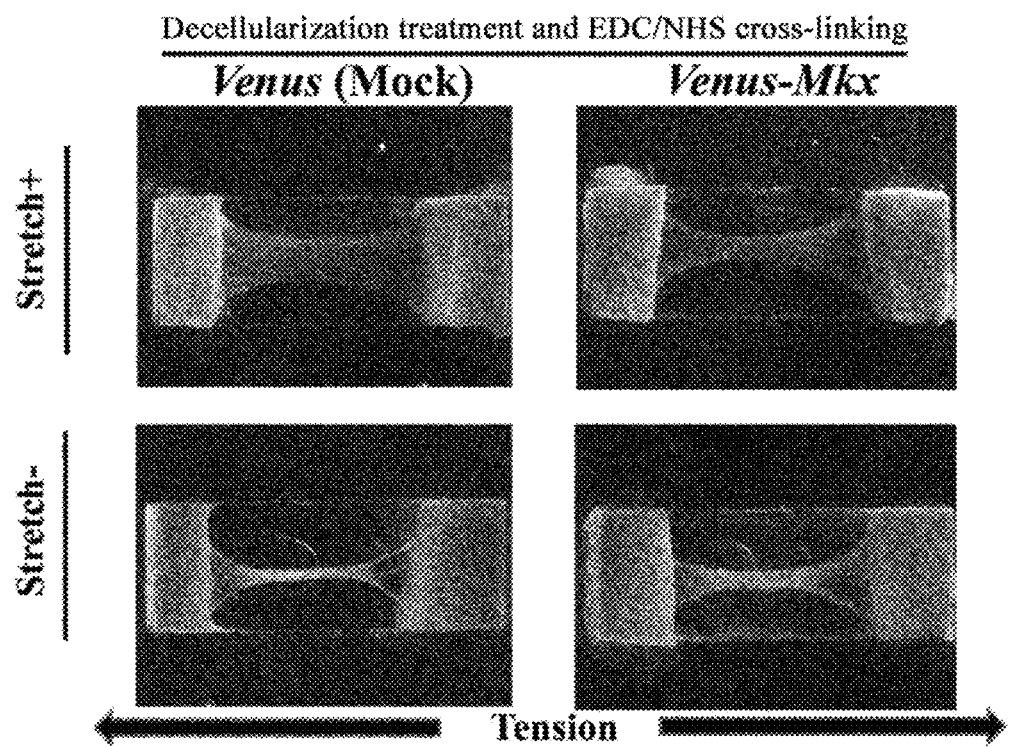
FIG. 5 shows an artificial C3H10T1/2-derived tendon ligament-like tissue that has been treated with decellularization and cross-linking.

The resulting decellularized cross-linked tendon ligament-like tissue is shown in FIG. 5. The decellularized cross-linked artificial tendon ligament-like tissue is produced in the artificial tendon ligament-like tissue applied with a stretch load using cells with forced Venus-Mkx expression (FIG. 5).

Figure 6:
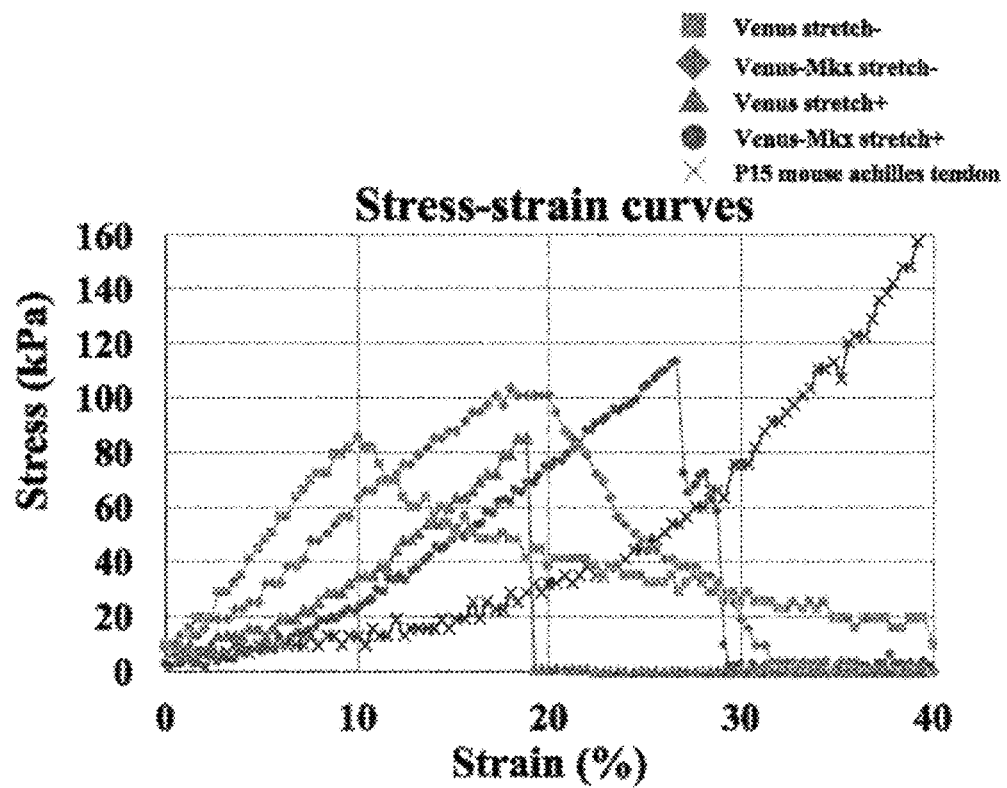
FIG. 6 shows the stress-strain curve (Stress-strain curve) during the intensity load test of an artificial C3H10T1/2-derived decellularized and cross-linked tendon ligament-like tissue. The vertical axis indicates stress (Stress), and the horizontal axis indicates strain (Strain). The breaking load was 113 kPa in the artificial tendon ligament-like tissue using cells with forced Venus-Mkx expression which has been applied with a stretch load, whereas the breaking load was 84 kPa in the control group applied with a stretch load. The breaking load was 103 kPa in the artificial tendon ligament-like tissue using cells with forced Venus-Mkx expression without application of stretch load, while the breaking load was 84 kPa in the control group that has been applied with a stretch load.

Intensity load test of the artificial tendon ligament-like tissue was carried out using a creep meter (Yamazaki, RE-33005B). Achilles tendon (P15 mouse Achilles tendon) from 15 neonatal mice was used as the positive control sample. The breaking load (ultimate tensile strength) was 113 kPa in the artificial tendon ligament-like tissue (Venus-Mkx stretch+) applied with a stretch load using cells with forced Venus-Mkx expression, whereas it was 84 kPa in the control group (Venus stretch+) applied with a stretch load. In addition, the breaking load was 103 kPa in the artificial tendon ligament-like tissue (Venus-Mkx stretch−) using cells with forced Venus-Mkx expression without stretch load, whereas the breaking load was 84 kPa in the control group applied with a stretch load (Venus stretch−) (FIG. 6 and Table 1).

TABLE 1

| | Elastin phase young's modulus (kPa) | Collagen phase young's modulus (kPa) | Ultimate tensile strength (kPa) |
|---|---|---|---|
| Venus stretch− | Measurement not available as J behavior curve was not observed | 847.8 | 84.8 |
| Venus-Mkx stretch− | Measurement not available as J behavior curve was not observed | 551.1 | 103.6 |
| Venus stretch+ | 241.5 | 642.2 | 84.8 |
| Venus-Mkx stretch+ | 141.3 | 676.9 | 113.4 |
| P15 mouse achilles tendon | 151.5 | 999.1 | 219.8 |

Example 3: Use of Mouse iPS Cells

Figure 7:
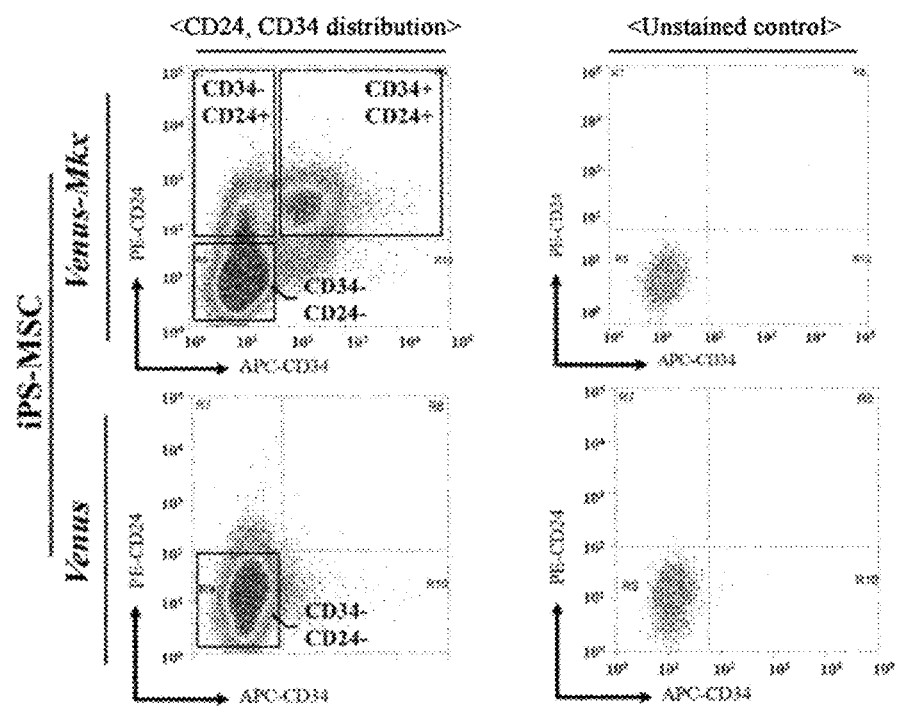
FIG. 7 shows the results of flow cytometry of iPS-MSCs with forced Venus-Mkx expression using an anti-CD24 antibody and anti-CD34 antibody. iPS-MSCs with forced Venus expression were used as control.

For murine embryonic fibroblasts, murine iPS cells were established by introducing Oct3/4, Sox2 and Klf4 retrovirally with reference to the method described in literature (Nakagawa M et al. 2008 Nat Biotechnol. 26 (1) 101-6). For the established iPS cells, induction of differentiation into mesodermal stem cells was performed using retinoic acid by referring to the method described in literature (Takashima Y et al. 2007 Cell. 129 (7) 1377-88). For mesodermal stem cells (iPS-MSCs) derived from the iPS cells produced by differentiation induction, the Venus-Mkx fusional gene was forcedly expressed using the retrovirus vector, and only the IPS-MSCs with forced Venus-Mkx expression were enriched by drug selection. For the established IPS-MSCs with forced Venus-Mkx expression, the $CD24^+CD34^+$ fraction was enriched with an anti-CD24 antibody and an anti-CD34 antibody using flow cytometry (BECKMAN COULTER, MoFlo XDP) with reference to literature (Rodeheffer, M S. et al. 2008 Cell. 135(17) 240-249), and tissue stem cells were isolated (FIG. 7).

Figure 8:
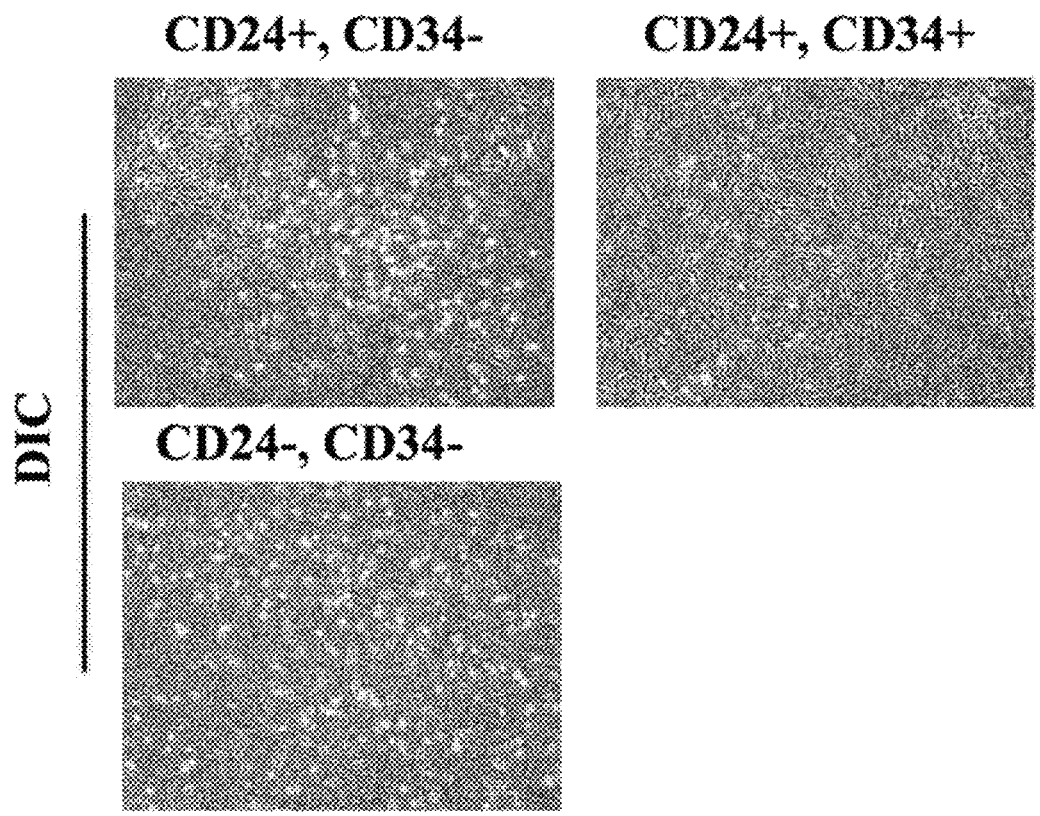
FIG. 8 shows an optical microscope image of iPS-MSCs with forced Venus-Mkx expression in various fractions isolated by flow cytometry.
Figure 9:
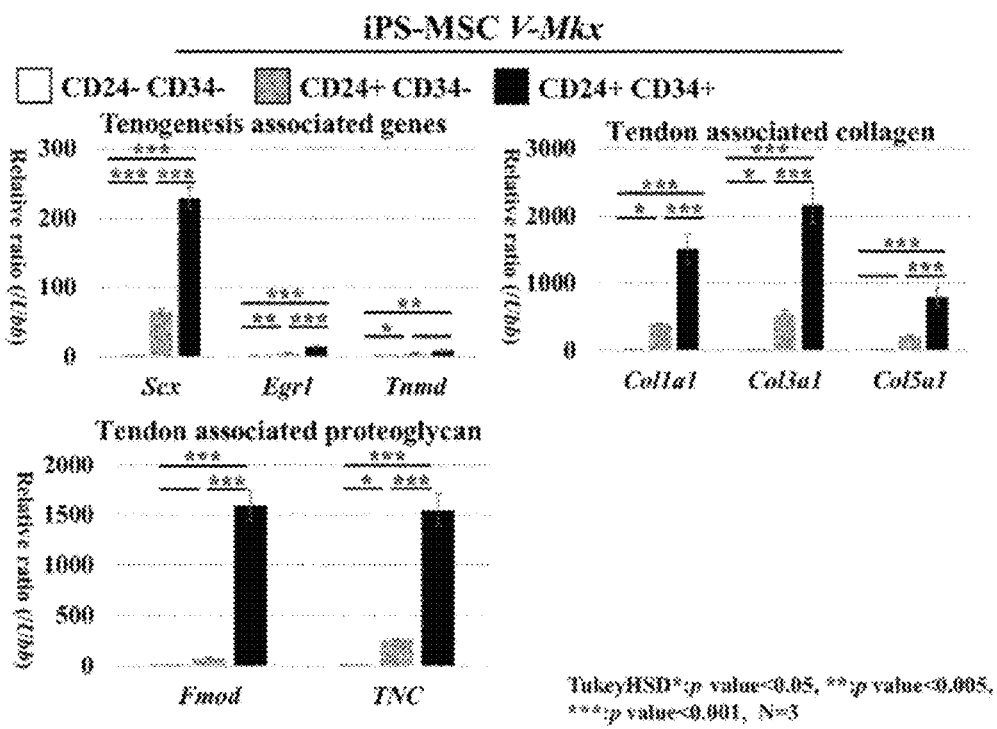
FIG. 9 shows the results of qRT-PCR analysis of tendon/ligament-related gene expression patterns of iPS-MSCs with forced Venus-Mkx expression in the fractions isolated by flow cytometry. The horizontal axis indicates the tendon ligament-related genes whose expressions were examined. The vertical axis indicates the levels of gene expression relative to the gene of comparison Ubb in the ΔΔcT assay in qRT-PCR.

The $CD24^+CD34^+$ fraction isolated from the iPS-MSCs with forced Venus-Mkx expression shows a uniform spindle-shaped morphology compared to the other fractions (FIG. 8). In addition, it was elucidated by the qRT-PCR method that the $CD24^+CD34^+$ fraction showed a stronger gene expression pattern of the tendon ligament than the other fractions (FIG. 9).

10 v/v % Collagen neutralize buffer (Nitta gelatin, Cellmatrix Type1-A), 10 v/v % MEMα (Gibco 12000-063 was suspended in DDW to make 10× the specified concentration), 10 v/v % FBS, 1 v/v % 100×NEAA (Gibco 11140-050), 1 v/v % GlutaMAX (Gibco 35050-061), and 1 v/v % 100× Pen Strep (Gibco 15140-122) were added to the collagen gel (Nitta gelatin, Cellmatrix Type1-A) to achieve the respective final concentrations described above. Further, with reference to literature (Laflamme, M A. et al. 2007 Nat Biotechnol. 25(9) 1015-24), the final concentrations of Z-VAD-FMK (G723A, PROMEGA, Bcl-Xl BH4 4-23 (197217-1MG, Calbiochem), Ciclosporin A (039-16301, Wako), Murine IGF-1 (250-19, PeoroTech), and Pinacidil monohydrate (sc-203198, ChemCruz) were adjusted to 100 mM, 50 nM, 200 nM, 100 ng/ml, and 50 mM, respectively, in order to enhance cell viability in the three-dimensional culture. These mixtures were used to suspend the $CD24^+CD34^+$ fraction ($5\times10^5$ cells) isolated from IPS-MSCs with forced Venus-Mkx expression. As a subject of comparison, the $CD24^-CD34^-$ fraction isolated from the IPS-MSCs with forced Venus-Mkx expression was used.

The mixture of gel and cells was injected into a three-dimensional stretch culture chamber (Strex, STB-3.5GS), incubated at 37° C. for 30 min in 5% $CO_2$, and turned into a gel. After gelation, an MEMα medium containing 10 v/v % FBS, 1 v/v % penicillin/streptomycin, 1 v/v % GlutaMAX (Gibco 35050-061, 1 v/v % 100×NEAA (Gibco 11140-050), and 55 μM 2-mercaptoethanol (Gibco 21985-023) was added to the chamber. After further incubation at 37° C. and 5% $CO_2$ for 18 hours to increase the intensity of the gel, stretching was performed using a cell-stretching device (Menicon Life Science, Shellpa Pro). Stretch load was carried out for 1 week, while the extension rate was gradually raised. Specifically, it was 2% (Day 1), 4% (Day 2), 5% (Day 3), 8% (Day 4), and 10% (Days 5-7), with a stretch time of 18 hours/day.

Figure 10:
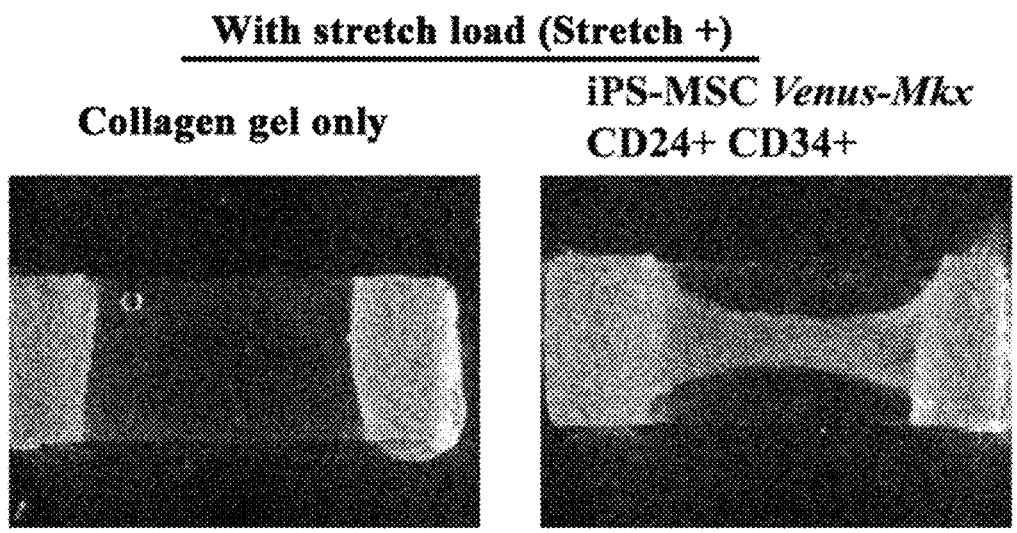
FIG. 10 is a photograph showing an artificial Venus-Mkx-derived tendon ligament-like tissue produced using collagen gel in a three-dimensional mechano-signaling cell culture system. The left column shows results for the control group with gel only. The right column is an artificial tendon ligament-like tissue using $CD24^+CD34^+$ cells transfected with Mkx.
Figure 11:
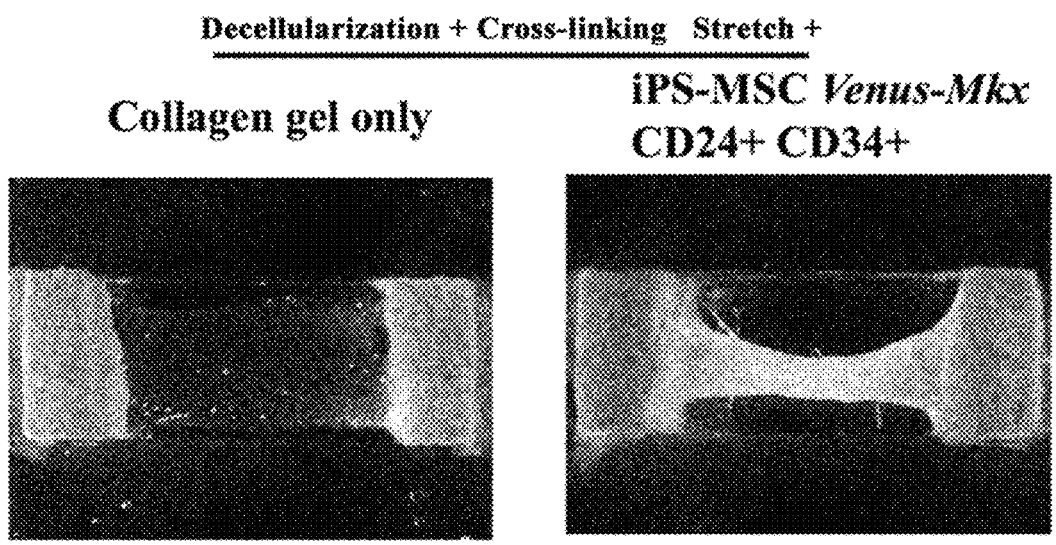
FIG. 11 shows an artificial tendon ligament-like tissue derived from iPS-MSCs with forced Venus-Mkx expression, which has been decellularized and cross-linked. The left column shows results for the control group with gel only.

The artificial tendon ligament-like tissue produced is shown in FIG. 10. An artificial tendon ligament-like tissue was produced in the artificial tendon ligament-like tissue applied with a stretch load using CD24+CD34+ IPS-MSCs with forced Venus-Mkx expression (FIG. 10).

Longitudinal sections of the tendon ligament-like tissue can be observed, for example, by electron microscopy (Hitachi, S-4500) in the tendon ligament-like tissue applied with a stretch load using CD24+CD34+ IPS-MSCs with forced Venus-Mkx expression.

Decellularization was performed on the artificial tendon ligament-like tissue using a high hydrostatic pressure method. Specifically, a cold isotropic pressure processing equipment (Kobe steel, Dr. CHEF) was used to press at 10,000 atmospheres, 15 minutes, and 10° C. After compression, the nuclei were washed with DNase (1 v/v % 10×DNase I Buffer (Takara Bio, 2270A), 10 U/ml Recombinant DNase I (RNase-free) (Takara Bio, 2270A), 1 v/v % penicillin/streptomycin) for three days and removed. Then, the DNase solution was washed with physiological saline for another three days, and the solution was removed.

For the artificial tendon-ligament-like tissue, cross-linking of the decellularized artificial tissue was performed to improve the stability of the artificial tissues in the body, by referring to literature (Nam, K. et al. 2009 J Artif Organs. 12(1) 47-54). The reaction was performed for 24 hours (in a 4° C. rotator) in a cross-linking reaction solution of 30% v/v ethanol/DDW, 70 mM EDC (wako 348-03631), and 70 mM NHS (wako 089-04032). Then, the reaction solution was removed by washing with DDW for one day.

The decellularized cross-linked artificial tendon ligament-like tissue derived from the prepared CD24+CD34+ IPS-MSCs with forced Venus-Mkx expression is shown. The decellularized cross-linked artificial tendon ligament-like tissue was produced in the artificial tendon ligament-like tissue applied with a stretch load using cells with forced Venus-Mkx expression (FIG. 12).

Intensity stress testing of the artificial tendon ligament-like tissue derived from CD24+CD34+ IPS-MSCs with forced Venus-Mkx expression was performed using, for example, a creep meter (Yamado, RE-33005B). Achilles tendon from neonatal mice on Day 15 is used as the positive control sample.

Example 4: Transplantation of the Artificial Tendon Ligament-Like Tissue into Adult Rats For the rat Achilles tendon, about 5 mm of the central part of the Achilles tendon on the gastrocnemius muscle side, which was considered to have a larger mass and contribute to the motion, was totally resected to create an injury model. The artificial tendon ligament-like tissue derived from CD24+CD34+ IPS-MSCs with forced Venus-Mkx expression, which was decellularized and nuclear washed, was transplanted using 7-0 sutures into the site of total excision of the Achilles tendon on the gastrocnemius muscle side for a model of Achilles tendon injury on the left gastrocnemius muscle side (FIG. 12). One week after the living donor transplantation, rats were given general anesthesia, and noninvasive imaging analysis of the injury site was performed using a microfocus X-ray device (Shimazu, Inc., inspeXio SMX-100CT) under the conditions of 100 kV tube voltage and 150 µA tube current. In the sham group (injury model group), there was a low-absorption area of X-ray transmission in the Achilles tendon, which can be presumed to be a result of interstitial tissue filling at the injury site, which differs from tendon tissues in radiolucency. In the meantime, the group transplanted with the artificial tendon ligament-like tissue derived from the CD24+CD34+ IPS-MSCs with forced Venus-Mkx expression showed the same uniform X-ray permeability as the control group (the non-invasion group). This indicates the possibility that in the group transplanted with the artificial tendon ligament-like tissue derived from CD24+CD34+ IPS-MSCs with forced Venus-Mkx expression, the tissue structure having the same physical characteristics towards X ray as the control group may be recovering during the repair process (FIG. 13).

Colonization of artificial tendon ligament-like tissue in adult rats is confirmed, for example, by the presence of migrating rat-derived cells in the transplanted decellularized tissue. In addition, the exercise load was imposed on the rat using a treadmill device, and a walking analysis by high speed camera (Logical Product, Sports Coaching CAM) was carried out in the artificial tendon ligament-like tissue transplantation group and the control group. The range of motion of the rat hind leg and walking distance of the rat were quantitatively analyzed.

Example 5: Use of Human iPS Cells

Human iPS cell 253G1 was received from the BioResource Center of the Institute of Physical and Chemical Research. The procedure described in the reference (Menendez L et al.) 2013 Nat Protoc. 8 (1) 203-12) was used to induce differentiation of the obtained iPS cells into mesodermal stem cells. Mesodermal stem cells of the iPS cell origin (iPS-MSCs) produced by differentiation induction were forced to express the Venus-Mkx fusional gene using a retrovirus vector, and only the IPS-MSCs with forced Venus-Mkx expression were enriched by drug selection. From the established IPS-MSCs with forced Venus-Mkx expression, the CD24+CD34+ fraction was concentrated using an anti-CD24 antibody and an anti-CD34 antibody using flow cytometry (BECKMAN COULTER, MoFlo XDP), and purification and homogenization of iPS cells were carried out.

Fibrinogen (SIGMA, F3879-1G), Thrombin (SIGMA, T6884-250UN), and Aprotinin (Wako, 010-23581) were adjusted to the final concentrations of 8.3 mg/ml, 33 U/ml, and 0.3 mg/ml, respectively, and the CD24+CD34+ IPS-MSCs with forced Venus-Mkx expression ($1\times10^7$ cells) were suspended using this mixture solution. As a subject of comparison, iPS-MSC cells that have been forced to express Venus using the retrovirus vector and selected with drugs, or CD24−CD34− IPS-MSCs with forced Venus-Mkx expression were used.

The mixture of gel and cells was injected into a three-dimensional stretch culture chamber (Strex, STB-3.5GS), incubated at 37° C. for 30 min in 5% $CO_2$, and turned into a gel. After gelation, an MEMα medium containing 10 v/v % FBS and 1 v/v % penicillin/streptomycin was added to the chamber. After further incubation at 37° C. and 5% $CO_2$ for 18 hours to increase the intensity of the gel, stretching was performed using a cell-stretching device (Menicon Life Science, Shellpa Pro). The stretch load was carried out for 1 week, while the extension rate was gradually raised. Specifically, it is 2% (Day 1), 4% (Day 2), 5% (Day 3), 8% (Day 4), and 10% (Days 5-7), with stretch time of 18 hours/day.

An artificial tendon ligament-like tissue was produced in the artificial tendon ligament-like tissue applied with a stretch load using CD24+CD34+ IPS-MSCs with forced Venus-Mkx expression.

Longitudinal sections of the artificial tendon ligament-like tissue were examined by electron microscopy (Hitachi, S-4500). Collagen fiber bundles parallel to the direction of extension were identified in the artificial tendon-ligamentlike tissue applied with a stretch load using CD24$^+$CD34$^+$ cells with forced Venus-Mkx expression.

The present specification shows the preferred embodiments of the present invention, and it is clear to those skilled in the art that such embodiments are provided simply for the purpose of exemplification. A skilled artisan may be able to make various transformations, and add modifications and substitutions without deviating from the present invention. It should be understood that the various alternative embodiments of invention described in the present specification may be used when practicing the present invention. Further, the contents described in all publications referred to in the present specification, including patents and patent application documents, should be construed as being incorporated the same as the contents clearly written in the present specification by their citation.

INDUSTRIAL APPLICABILITY

The present inventors have successfully created an in vitro artificial tissue with cells and collagen fibers oriented parallel to the direction of elongation, which has not been observed in conventional culture systems. The present invention allows a tendon/ligament regenerative medicine approach and may be very useful in the treatment of patients with injured tendons/ligaments.

The invention claimed is:

1. A method of manufacturing an artificial tendon/ligament-like tissue, the method comprising: (a) embedding a collagen-secreting cell in a gel that is strong enough to withstand a tensile load, and (b) culturing the cell while applying the tensile load to the gel, wherein the applying of the tensile load comprises gradually increasing an extension rate of the gel each day of the culturing.

2. The method according to claim 1, wherein the collagen-secreting cell is a cell that constitutively expresses the Mkx gene.

3. The method according to claim 1, wherein the collagen-secreting cell is a cell that has been transfected with a vector to introduce the Mkx gene.

4. The method according to claim 1, wherein the cell is a C3H10T1/2 cell, a cell line, a normal cell, a cell derived from a tissue stem cell, a cell derived from an ES cell, or a cell derived from an iPS cell.

5. The method according to claim 1, wherein the cell is CD24 positive and CD34 positive.

6. The method according to claim 3, wherein the vector is a retroviral vector.

7. The method according to claim 1, wherein the gel is a fibrin gel.

8. The method according to claim 1, wherein the gel contains a plasmin inhibitor.

9. The method according to claim 1, wherein the gel contains aprotinin.

10. The method according to claim 1, wherein the tensile load is at least 2% extension per day.

11. The method according to claim 1, further comprising (c) performing a decellularization treatment on the gel subsequent to the culturing of the cell.

12. The method according to claim 11, wherein the decellularization treatment comprises microwave irradiation.

13. A method of manufacturing an artificial tendon/ligament-like tissue, the method comprising: (a) embedding an isolated CD24$^+$/CD34$^+$ collagen-secreting cell in a gel, and (b) culturing the cell while applying a tensile load to the gel.

14. The method according to claim 13, wherein the cell is a cell derived from a tissue stem cell, a cell derived from an ES cell, or a cell derived from an iPS cell.

15. The method according to claim 14, wherein the cell is a mesodermal stem cell, and the method further comprises inducing differentiation of the ES cell or the iPS cell into the mesodermal stem cell.

* * * * *